United States Patent [19]

Müller

[11] 4,434,171

[45] Feb. 28, 1984

[54] DIBENZAZEPINE DERIVATIVES, PHARMACEUTICAL COMPOSITIONS CONTAINING THEM, AND PHARMACEUTICAL METHODS USING THEM

[75] Inventor: Werner Müller, Gümligen, Switzerland

[73] Assignee: Sandoz Ltd., Basel, Switzerland

[21] Appl. No.: 323,759

[22] Filed: Nov. 23, 1981

[30] Foreign Application Priority Data

Nov. 28, 1980 [CH] Switzerland ................. 8829/80

[51] Int. Cl.³ .................. A61K 31/445; C07D 401/04
[52] U.S. Cl. ................................. 424/267; 260/244.4
[58] Field of Search ..................... 260/244.4, 239 D; 424/267

[56] References Cited

U.S. PATENT DOCUMENTS

| | | | |
|---|---|---|---|
| 2,802,007 | 8/1957 | Biel | 546/185 |
| 3,038,896 | 6/1962 | Habicht et al. | 260/239 |
| 3,079,394 | 2/1963 | Dowbenko | 546/185 X |
| 3,153,652 | 10/1964 | Drukker et al. | 424/267 |
| 3,403,159 | 9/1968 | Pesson | 546/185 |
| 3,894,001 | 7/1975 | Drukker | 424/267 X |
| 3,928,356 | 12/1975 | Umio et al. | 424/267 X |
| 4,045,445 | 8/1977 | Hardy, Jr. et al. | 260/244.4 |
| 4,081,450 | 3/1978 | Zimmerman | 546/185 |
| 4,221,715 | 9/1980 | McKenzie et al. | 260/244.4 |
| 4,360,525 | 11/1982 | Müller | 424/267 |

FOREIGN PATENT DOCUMENTS

| | | |
|---|---|---|
| 26469 | 4/1981 | European Pat. Off. |
| 1136706 | 4/1963 | Fed. Rep. of Germany |
| 96408 | 7/1968 | France |
| 50-12439 | 5/1975 | Japan ................. 260/244.4 |

OTHER PUBLICATIONS

Rice, J. Org. Chem. vol. 40(12), pp. 1850–1851, (1975).
Olofson, et al., Tetrahedron Letters, No. 18, pp. 1567–1570, (1977).
Protiva, et al., Chemical Abstracts, vol. 66, 55414f (1967).
Werner, et al., J. Med. Chem., vol. 8, pp. 74–80, (1965).
Werner, Chemical Abstracts, vol. 61, 4326e, (1961) (V).
Jilek, et al., Chemical Abstracts, vol. 62, 14707d(1965).
Bürki, et al., Eur. J. Med. Chem., vol. 13(5), pp. 479–485, (1978).
Kovar, et al., Coll. Czech. Chem. Comm., vol. 43, pp. 2068–2081, (1978).
Schmutz, Arzneim.-Forsch., (Drug Res.), 25, No. 5, pp. 712–720, (1975).

*Primary Examiner*—Donald G. Daus
*Assistant Examiner*—Diana G. Rivers
*Attorney, Agent, or Firm*—Gerald D. Sharkin; Robert S. Honor; Joseph J. Borovian

[57] ABSTRACT

Dibenzazepine derivatives in free base form or in pharmaceutically acceptable acid addition salt form are useful as neuroleptic, antidepressant, sleep-inducing, sleep-promoting and sleep-prolonging agents.

8 Claims, No Drawings

DIBENZAZEPINE DERIVATIVES, PHARMACEUTICAL COMPOSITIONS CONTAINING THEM, AND PHARMACEUTICAL METHODS USING THEM

The present invention relates to dibenzazepine derivatives, their production and pharmaceutical compositions containing them.

The present invention provides 5,6-dihydro-5-(4-piperidinyl)-11H-dibenz[b,e]azepines.

These compounds are hereinafter referred to as compounds of the invention.

The present invention further provides a compound of formula I,

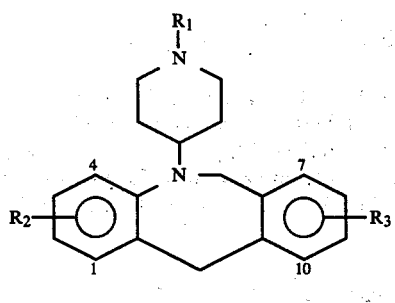

wherein
$R_1$ is hydrogen, $C_{1-4}$-alkyl, $C_{2-5}$-alkyl substituted by cyano, $C_{7-9}$-phenylalkyl, $C_{3-6}$-cycloalkyl or $C_{4-7}$-cycloalkylalkyl, $C_{2-5}$-hydroxyalkyl or a physiologically acceptable hydrolyzable ester thereof, and
$R_2$ and $R_3$ are, independently of each other, hydrogen, halogen, trifluoromethyl, $C_{1-4}$-alkyl, $C_{1-4}$-alkoxy or $C_{1-4}$-alkylthio.

In formula I any alkyl, alkoxy or alkylthio radical of 1 to 4 carbon atoms, has preferably 1 to 3 carbon atoms, especially 1 and 2 carbon atoms. The alkyl moiety of cyanoalkyl, hydroxyalkyl, phenylalkyl or cycloalkylalkyl has preferably 2 or 3 carbon atoms. Preferably the hydroxy group in free form or in esterified form or the cyano group is attached to a carbon atom other than the carbon atom adjacent to the nitrogen atom. Substituted alkyl, e.g. cyanoalkyl, hydroxyalkyl, phenylalkyl or cycloalkylalkyl, has the substituent preferably in the terminal distal position. Cycloalkyl or the cycloalkyl moiety of cycloalkylalkyl is conveniently cyclopentyl and especially cyclopropyl. The alkyl moiety of cycloalkylalkyl has conveniently 1 carbon atom. Halogen means fluorine, chlorine, bromine or iodine. Halogen is conveniently fluorine, chlorine or bromine, preferably fluorine or chlorine.

Physiologically acceptable hydrolyzable esters are those esters which under physiological conditions are split to the corresponding compounds having a hydroxyalkyl piperidinyl group. Such esters are particularly derived from ($C_{2-18}$)alkanoic, ($C_{3-7}$)cycloalkylcarboxylic, benzoic, phenyl($C_{2-7}$)alkanoic or benzoic or phenyl($C_{2-7}$)alkanoic acids, monosubstituted in the phenyl ring by ($C_{1-4}$)alkyl or mono- or independently disubstituted in the phenyl ring by halogen, or mono- or independently di- or independently tri-substituted in the phenyl ring by ($C_{1-4}$)alkoxy.

$R_1$ is preferably alkyl. $R_2$ is preferably hydrogen. When $R_2$ is other than hydrogen, it is conveniently in position 2 or 3, especially 3. $R_3$ is preferably halogen. $R_3$ is conveniently in position 8 or 9, especially 8.

The present invention in another aspect provides a process for the production of a compound of the invention which comprises (a) reducing a 4-(5,6-dihydro-11H-dibenz[b,e]azepin-5-yl)-1-substituted pyridinium salt to obtain a 5,6-dihydro-5-(4-piperidinyl)-11H-dibenz[b,e]azepine substituted at the piperidine nitrogen or (b) splitting off the alkyl or benzyl group from 5,6-dihydro-5-(1-alkyl or 1-benzyl-4-piperidinyl)-11H-dibenz[b,e]azepine to produce derivatives unsubstituted at the piperidine nitrogen.

In particular a compound of formula I as defined above may be produced by a process which comprises (a) obtaining a compound of formula Ia,

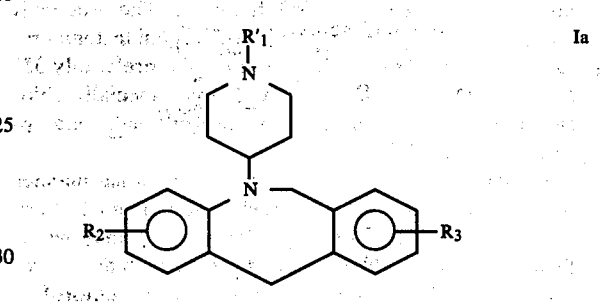

wherein $R_2$ and $R_3$ are as defined above, and $R_1'$ has the same significance as $R_1$ other than hydrogen, by reducing a compound of formula II,

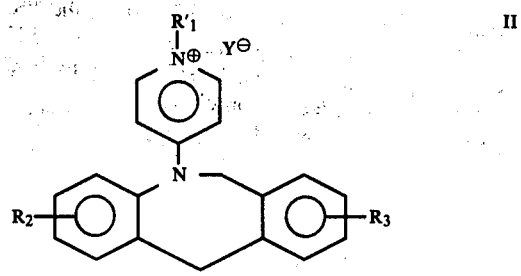

wherein $R_1'$, $R_2$ and $R_3$ are as defined above and Y is an anion, or (b) obtaining a compound of formula Ib,

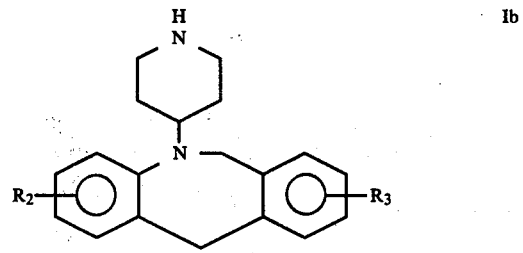

wherein $R_2$ and $R_3$ are as defined above, by splitting off a group $R_1''$ in a compound of formula Ib'

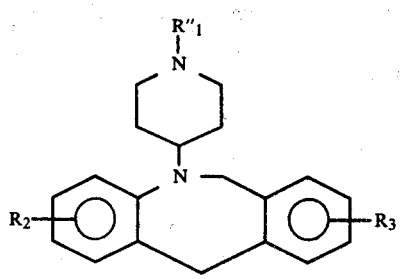

wherein $R_2$ and $R_3$ are as defined above and $R_1''$ is $(C_{1-4})$alkyl or benzyl.

Process (a) may be carried out using appropriate reducing agents for N-substituted pyridinium salts, e.g. sodium borohydride in a mixture of water and a water-miscible solvent, such as diethylene glycol dimethyl ether or ethylene glycol dimethyl ether. The process is conveniently effected at a pH 6-7. Suitable temperatures are from about 20° to about 65° C., preferably 35° to 45° C. Y is for example a halide ion, especially chloride, bromide or iodide or an arylsulfonate, e.g. p-toluolsulfonate.

Process (b) may be effected in conventional manner for splitting off alkyl or benzyl groups from tertiary amines. The dealkylation or debenzylation may be effected with halogen formic acid esters, such as chloroformate, e.g. ethyl, vinyl, phenyl or benzyl chloroformate in a solvent such as 1,2-dichloroethane at room temperature. Conveniently an acid binding agent is present, e.g. potassium carbonate or a mixture of the latter with a steric hindered trialkylamine, such as ethyl diisopropyl amine. The hydrolysis of the resulting urethane can be effected for example with alcoholic hydrogen chloride at reflux temperature of the mixture.

The benzyl group may also be split off by hydrogenolysis, e.g. using palladium on charcoal.

Compounds of formula II may, for example, be prepared by reacting a compound of formula III,

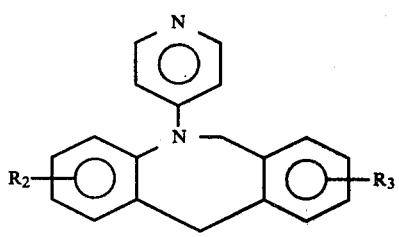

with a compound of formula IV, $R_1'$—Y            IV

The reaction may be carried out in a polar solvent, e.g. acetonitrile, isopropanol or dimethylformamide. Suitable temperatures are from 20° to the reflux temperature of the solvent, preferably 20° to 40° C. When $R_1'$ is hydroxyalkyl, this group is conveniently protected temporarily by a protective group, e.g. acetyl, which is then split off thereafter.

Compounds of formula III may, for example, be obtained by reacting a compound of formula V,

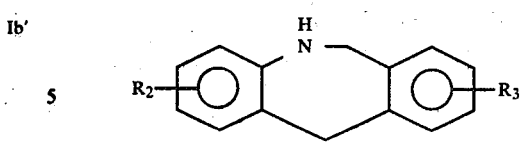

with a compound of formula VI,

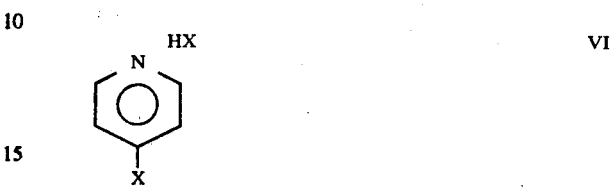

wherein both radicals X are independently chlorine or bromine.

The reaction is conveniently effected in the absence of a solvent at temperatures between 130° and 210°, preferably 160° and 190° C.

Compounds of formula V may, for example, be prepared by reducing a compound of formula VII,

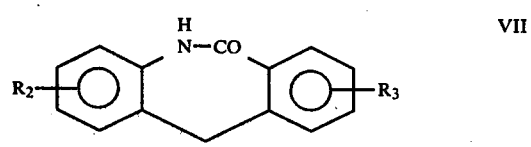

4-(5,6-Dihydro-11H-dibenz[b,e]azepin-5-yl)-1-substituted pyridinium salts other than those of formula II may be obtained in analogous manner to that described above for compounds of formula II.

Insofar as the production of starting materials is not particularly described these compounds are known or may be produced in analogous manner to known compounds or to processes described herein.

Free base forms of the compounds of the invention may be converted into acid addition salt forms in conventional manner and vice versa. Suitable acids include, for example, hydrochloric acid, hydrobromic acid, maleic acid, fumaric acid and succinic acid.

In the following examples all temperatures are given in degrees Centigrade and are uncorrected.

EXAMPLE 1

8-Chloro-5,6-dihydro-5-(1-methyl-4-piperidinyl)-11H-dibenz[b,e]azepine

To a stirred suspension of 1.25 g sodium borohydride in 10 ml diethylene glycol dimethyl ether is added dropwise at 35° a solution of 3.0 g 4-(8-chloro-5,6-dihydro-11H-dibenz[b,e]azepin-5-yl)-1-methyl-pyridinium-iodide in 33 ml diethylene glycol dimethyl ether/water (10:1). Stirring is continued at a temperature of 35° for 3 hours. The mixture is acidified with diluted hydrochloric acid and evaporated. The residue is made alkaline with sodium hydroxide and extracted with methylene chloride. The organic phase is dried and evaporated.

Solution in ethanol, addition of an equimolar amount of maleic acid, followed by addition of ether yields the heading compound in maleate salt form, m.p. 182°-185°.

The starting material 4-(8-chloro-5,6-dihydro-11H-dibenz[b,e]azepin-5-yl)-1-methyl pyridinium iodide may be obtained as follows:

(a) 8-chloro-5,6-dihydro-11H-dibenz[b,e]azepine

To a suspension of 1.5 g lithium aluminium hydride in 100 ml tetrahydrofuran is added with ice cooling first 1.05 ml chloroform and thereafter portionwise 3.0 g of 8-chloro-5,6-dihydro-11H-dibenz[b,e]azepin-6-one. The mixture is stirred at room temperature for 15 hours. To the mixture is then added dropwise under ice cooling 9.0 ml of a saturated solution of potassium carbonate. The precipitate is filtered off and washed with ether. The filtrate is then evaporated and the residue recrystallised from methylene chloride/ether/petroleum ether to give the heading compound, m.p. 132°–135°.

(b) 4-(8-chloro-5,6-dihydro-11H-dibenz[b,e]azepin-5-yl)-1-methyl pyridinium iodide A mixture of 1.5 g 8-chloro-5,6-dihydro-11H-dibenz[b,e]azepine and 5.1 g 4-bromo-pyridine hydrochloride is heated at 185° for 4 hours. 2 N hydrochloric acid and ether are added. The acid phase is made alkaline with sodium hydroxide and extracted with methylene chloride. The organic phase is dried and evaporated. The residue is chromatographed on a 15-fold amount of silica gel with methylene chloride/methanol/conc. ammonia (9:1:0.1). The fractions with the main product 4-(8-chloro-5,6-dihydro-11H-dibenz[b,e]azepin-5-yl)pyridine are evaporated. The residue (1.0 g) dissolved in 12 ml acetonitrile and treated at 40° with 1.0 ml methyl iodide. The mixture is stirred at room temperature for 90 minutes and then evaporated in vacuo to give the heading compound as a yellow oil.

EXAMPLE 2

In analogous manner to that described in Example 1, the following compounds of formula I are obtained:

| Example | $R_1$ | $R_2$ | $R_3$ | m.p.* |
|---|---|---|---|---|
| a | $CH_3$ | H | H | 147–151 |
| b | $CH_3$ | 3-Cl | H | 198–202 |
| c | $CH_3$ | H | 8-F | 193–197 |

*maleate

EXAMPLE 3

In analogous manner to that described in Example 1, the following compounds of formula I may be obtained:

| Example | $R_1$ | $R_2$ | $R_3$ |
|---|---|---|---|
| a | $-(CH_2)_2OCOC_{17}H_{35}$ | 3-Cl | H |
| b | $-CH_2-\triangleleft$ | 3-F | H |
| c | $n-C_3H_6OH$ | H | 8-S—$iC_3H_7$ |
| e | $-CH_2CH_2-\diamondsuit$ | 3-$CF_3$ | 8-$OC_2H_5$ |
| f | $C_3H_6CN$ | 2-$C_3H_7$ | 8-$CF_3$ |

EXAMPLE 4

The following esters of the compounds of formula I may be obtained:

| Example | $R_1$ | $R_2$ | $R_3$ |
|---|---|---|---|
| a | $C_3H_6OCO$—n-nonyl | H | 8-$CF_3$ |
| b | $C_4H_8OCO$—(3-ethylbenzyl) | 2-$OCH_3$ | H |

The compounds of the invention are useful because they possess pharmacological activity in animals and are therefore useful as pharmaceuticals, e.g. for therapy. In particular, the compounds of the invention are useful as neuroleptic agents in the treatment of e.g. psychotic disturbances such as schizophrenia, as indicated in standard tests, e.g. by an inhibition of spontaneous motor activity in male mice on p.o. administration of from about 1 to about 50 mg/kg animal body weight of the compounds e.g. in accordance with the principles of Caviezel and Baillod (Pharm. Acta Helv. (1958), 33, 465–484).

Additionally the compounds on administration to mice of from about 0.1 to about 10 mg/kg i.p. inhibit the hypermotility induced by 4,α-dimethyl-m-tyramine (H 77/77) in a test carried out according to the principles of C. Rüdeberg, Psychopharmacology 59, 247–254 (1978). At a concentration of about 10 to 1000 nM the compounds bind to $^3$H-Spiperone receptors as can be shown in a modified test from J. Leysen et al., Biochem. Pharmacol. 27, 307–316 (1978):

Fresh calf brain striatal tissue is homogenized in a 25 fold volume of Tris buffer (50 mM, pH 7.7, 120 mM sodium chloride) and centrifuged. The pellets are resuspended in a 22 fold volume of the Tris buffer, incubated for 15 min. at 37° C., recentrifuged and the pellets resuspended in a 300 fold volume of the Tris buffer. The composition of the assay mixtures (total volume=2 ml) is as follows: 45 mM Tris buffer pH 7.7, 108 mM sodium chloride, membranes corresponding to 6 mg of original tissue weight, 0.1 nM $^3$H-Spiperone, $5 \times 10^{-7}$ M Cinanserin to eliminate the contribution of 5 $HT_2$-receptors to Spiperone binding and 1 uM of unlabelled Spiperone. To assess the potency of drugs in inhibiting specific Spiperone binding (difference between total and non-specific binding), the test compounds are added to give 5 to 9 different concentrations between 1 nM and 10 uM, each in duplicate. After incubation for 40 min. at room temperature, the assay mixtures are rapidly filtered through Whatman GF/B filters and washed twice with 5 ml of ice cold Tris buffer and then scintillation-counted.

For the above mentioned use the dosage will, of course, vary depending on the compound employed, mode of administration and therapy desired. However, in general, satisfactory results are obtained with a daily dosage of from about 0.2 mg to about 100 mg per kg animal body weight, conveniently given in divided doses 2 to 4 times a day or in sustained release form. For the larger mammals, the total daily dosage is in the range from about 25 mg to about 600 mg (e.g. from 25 mg to about 100 mg), and dosage forms suitable for oral administration comprise from about 6 mg to about 300 mg (e.g. 6 to 50 mg) of the compounds admixed with a solid or liquid pharmaceutical carrier or diluent.

The compounds of the invention are further useful as anti-depressant agents as indicated in standard tests, for example, by an inhibition of tetrabenazine-induced catalepsy and ptosis in rats on intraperitoneal administration of from 5 to 15 mg per kilogram animal body weight of the compound in accordance with the method described by Stille (Arzneimittel-Forsch. 1964, 14, 534).

For this use the dosage will, of course, vary depending on the compound employed, mode of administration and condition to be treated. However, in general satisfactory results are obtained with a daily dosage of from about 0.1 to about 15 mg per kg animal body weight, preferably given in divided doses 2 to 4 times a day, or in sustained release form. For the larger mammals the total daily dosage is in the range from about 10 to about 500 mg and dosage forms suitable for oral administration comprise from about 2 to about 250 mg of the compound admixed with a solid or liquid pharmaceutical carrier or diluent.

Additionally the compounds of the invention are useful as sleep-inducing, sleep-promoting and sleep-prolonging agents, as indicated in standard-tests. For example, in one test according to the principles of H. Kleinlogel, European J. Pharmacol. 33, 159–163 (1975) an increase in the sleep phase II and a decrease of the wake phase is observed after administration to rats of from 0.5 to 80 mg/kg p.o. animal body weight of the compounds.

For this use the dosage will, of course, vary depending on the compound employed, mode of administration and therapy desired. However, in general, satisfactory results are obtained with a daily dosage of from 0.1 mg to about 80 mg per kg animal body weight, conveniently given shortly before retiring to sleep. For the larger mammals, the total dasily dosage is in the range from about 10 to about 100 mg. Examples of unit dosage forms for the larger mammals are from 2 to 50 mg.

The neuroleptic activity is the preferred utility. The preferred compound is the Example 1 compound.

The compounds of formula I may be administered in similar manner to known standards for use in these utilities, for example for the neuroleptic activity, Clozapine. The suitable dasily dosage for a particular compound will depend on a number of factors such as its relative potency of activity. It has for example been determined that the preferred compound of this invention, the Example 1 compound has an $IC_{50}$ of 100 nM in the above described neuroleptic test from J. Leysen as compared to an $IC_{50}$ of 668 nM for Clozapine in this test. The activity of the Example 1 compound in inhibiting spontaneous motor activity in mice on p.o. administration is comparable to that of Clozapine. It is therefore indicated that this compound may be administered at similar or lower dosages than conventionally employed for Clozapine for the neuroleptic indication.

The compounds of the invention may be administered in pharmaceutically acceptable acid addition salt form. Such acid addition salts forms exhibit the same order of activity as the free base forms. The present invention also provides a pharmaceutical composition comprising a compound of the invention, in free base form or in pharmaceutically acceptable acid addition salt form, in association with a pharmaceutical carrier or diluent. Such compositions may be in the form of, for example, a solution or a tablet.

A group of compounds comprises those wherein $R_1$ is alkyl and $R_2$ and $R_3$ are independently hydrogen or halogen.

In a first group of compounds $R_1$ is hydrogen.
In a second group of compounds $R_1$ is alkyl.
In a third group of compounds $R_1$ is alkyl substituted by cyano.
In a fourth group of compounds $R_1$ is phenylalkyl.
In a fifth group of compounds $R_1$ is cycloalkyl.
In a sixth group of compounds $R_1$ is cycloalkylalkyl.
In a seventh group of compounds $R_1$ is hydroxyalkyl.
In an eighth group of compounds $R_2$ is hydrogen.
In a ninth group of compounds $R_2$ is halogen.
In a tenth group of compounds $R_2$ is trifluoromethyl.
In an eleventh group of compounds $R_2$ is alkyl.
In a twelfth group of compounds $R_2$ is alkoxy.
In a thirteenth group of compounds $R_2$ is alkylthio.
In a fourteenth group of compounds $R_3$ is hydrogen.
In a fifteenth group of compounds $R_3$ is halogen.
In a sixteenth group of compounds $R_3$ is trifluoromethyl.
In a seventeenth group of compounds $R_3$ is alkyl.
In an eighteenth group of compounds $R_3$ is alkoxy.
In a nineteenth group of compounds $R_3$ is alkylthio.

I claim:

1. A compound of formula I

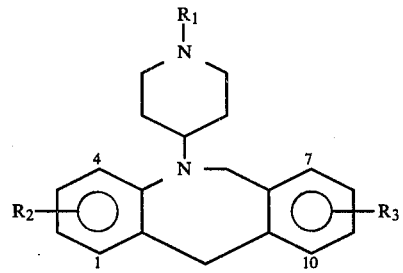

wherein
$R_1$ is hydrogen, $C_{1-4}$-alkyl, $C_{2-5}$-alkyl substituted by cyano, $C_{7-9}$-phenylalkyl, $C_{3-6}$-cycloalkyl or $C_{4-7}$-cycloalkylalkyl, $C_{2-5}$-hydroxyalkyl or a physiologically acceptable hydrolyzable ester thereof, and
$R_2$ and $R_3$ are, independently of each other, hydrogen, halogen, trifluoromethyl, $C_{1-4}$-alkyl, $C_{1-4}$-alkoxy or $C_{1-4}$-alkylthio,
in free base form or in a pharmaceutically acceptable acid addition salt form.

2. A compound according to claim 1 wherein $R_1$ is $C_{1-4}$alkyl, and $R_2$ and $R_3$ are, independently, hydrogen or halogen.

3. A compound of claim 1 which is 5-(1-methyl-4-piperidinyl)-5,6-dihydro-11H-dibenz[b,e]azepine in free base form or in a pharmaceutically acceptable acid addition salt form.

4. A compound of claim 1 which is 3-chloro-5,6-dihydro-5-(1-methyl-4-piperidinyl)-11H-dibenz[b,e]azepine in free base form or in a pharmaceutically acceptable acid addition salt form.

5. A compound of claim 1 which is 8-fluoro-5,6-dihydro-5-(1-methyl-4-piperidinyl)-11H-dibenz[b,e]azepine in free base form or in a pharmaceutically acceptable acid addition salt form.

6. A compound of claim 1 which is 8-chloro-5,6-dihydro-5-(1-methyl-4-piperidinyl)-11H-dibenz[b,e]azepine in free base form or in a pharmaceutically acceptable acid addition salt form.

7. A method of inducing or promoting or prolonging sleep or treating psychotic disturbances or depressions, which comprises administering a therapeutically effective amount of a compound of claim 1 in free base form or in a pharmaceutically acceptable acid addition salt form to a subject in need of such treatment.

8. A pharmaceutical composition useful in inducing, promoting or prolonging sleep or in treating psychotic disturbances or depressions comprising a pharmaceutically acceptable carrier or diluent and a therapeutically effective amount of a compound of claim 1 in free base form or in a pharmaceutically acceptable acid addition salt form.

* * * * *